United States Patent
Valenzuela Beck et al.

(10) Patent No.: US 11,583,201 B2
(45) Date of Patent: Feb. 21, 2023

(54) DEVICE FOR RECORDING THE VASCULAR RESPONSE OF THE HUMAN SPINAL CORD TRIGGERED BY A SUPRASENSIBLE STIMULUS THROUGH THE USE OF FUNCTIONAL NEAR-INFRARED SPECTROSCOPY

(71) Applicant: PONTIFICIA UNIVERSIDAD CATOLICA DE CHILE, Santiago (CL)

(72) Inventors: Felipe Ignacio Valenzuela Beck, Santiago (CL); Sergio Andres Uribe Arancibia, Santiago (CL); Antonio Alejandro Eblen Zajjur, Santiago (CL); Ranganatha Sitaram, Santiago (CL); Mohit Rana, Tuebingen (DE)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 213 days.

(21) Appl. No.: 16/958,433

(22) PCT Filed: Dec. 27, 2018

(86) PCT No.: PCT/CL2018/050155
§ 371 (c)(1),
(2) Date: Jun. 26, 2020

(87) PCT Pub. No.: WO2019/126898
PCT Pub. Date: Jul. 4, 2019

(65) Prior Publication Data
US 2021/0052172 A1    Feb. 25, 2021

(30) Foreign Application Priority Data
Dec. 28, 2017    (CL) .................................. 3462-2017

(51) Int. Cl.
*A61B 5/00* (2006.01)
*A61B 5/026* (2006.01)
*A61N 1/36* (2006.01)

(52) U.S. Cl.
CPC ........ *A61B 5/0261* (2013.01); *A61N 1/36034* (2017.08); *A61B 2562/0233* (2013.01)

(58) Field of Classification Search
CPC .................. A61B 5/0261; A61B 5/026; A61B 2562/0233; A61B 5/0075; A61B 5/407;
(Continued)

(56) References Cited

U.S. PATENT DOCUMENTS

2009/0062685 A1* 3/2009 Bergethon ............... A61B 5/24
600/554
2009/0062885 A1 3/2009 Brighton
(Continued)

FOREIGN PATENT DOCUMENTS

KR    20140052781 A    5/2014

*Primary Examiner* — Scott M. Getzow
(74) *Attorney, Agent, or Firm* — Raphael Bellum PLLC

(57) ABSTRACT

The invention consists of a device to evaluate hemodynamic response generated by the spinal cord in response to a suprasensorial stimulus applied to a peripheral nerve (medium or posterior tibial) by the use of functional near-infrared spectroscopy (fNIRS). The device consists of 3 main components, an electrical stimulator, an optical recording unit and a signal processing and control module. The device allows non-invasive, comfortable, harmless, portable, home-based, and low-cost evaluation of changes in local hemodynamic parameters in response to neuronal activation of the spinal cord by electrical stimulation of a peripheral nerve. The invention also includes a corresponding method of using the device and monitoring the spinal function.

10 Claims, 1 Drawing Sheet

(58) Field of Classification Search
CPC ... A61B 5/6832; A61B 5/4052; A61B 5/6823; A61B 5/14552; A61N 1/36034
See application file for complete search history.

(56) References Cited

U.S. PATENT DOCUMENTS

| | | |
|---|---|---|
| 2010/0105998 A1 | 4/2010 | Benni |
| 2014/0343384 A1 | 11/2014 | Floyd |
| 2018/0199849 A1* | 7/2018 | Axelrod .................. A61B 5/08 |

* cited by examiner

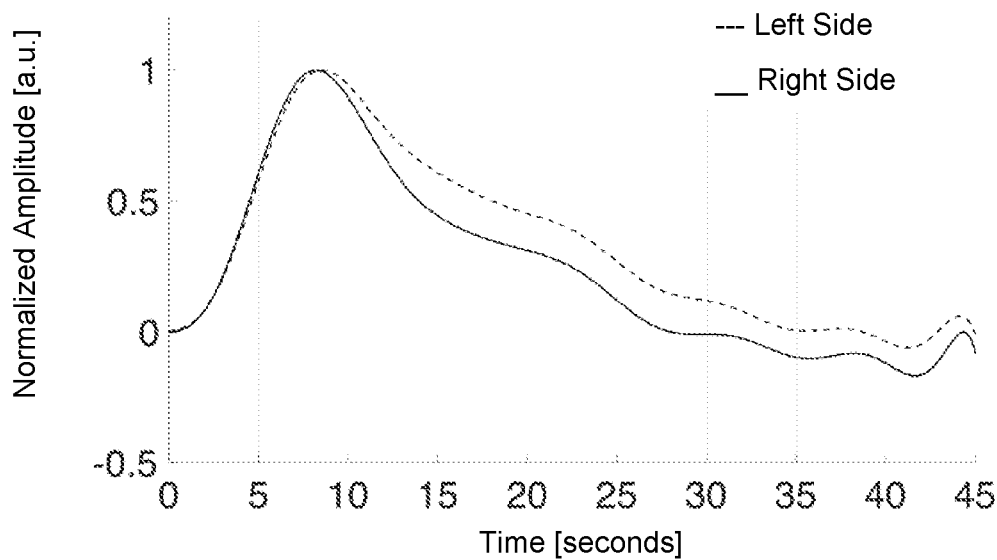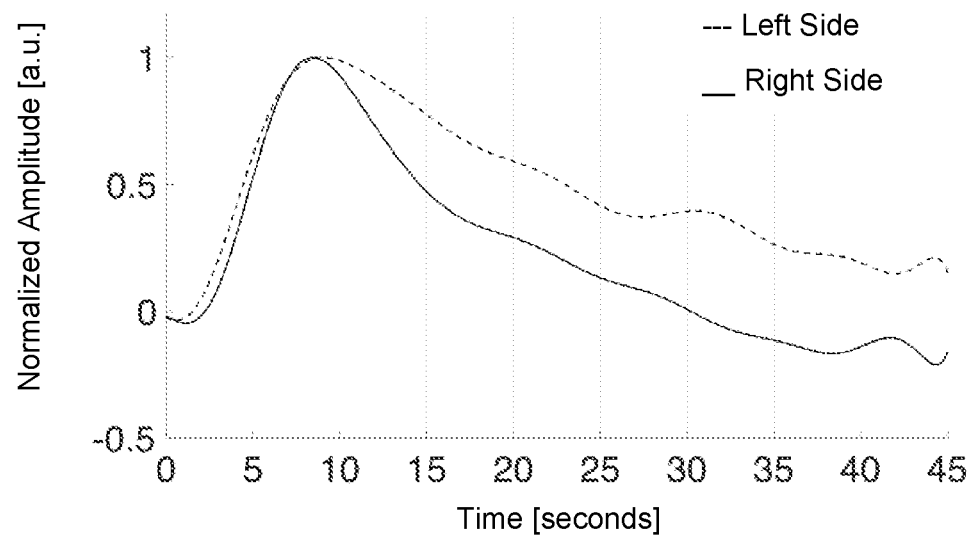

DEVICE FOR RECORDING THE VASCULAR RESPONSE OF THE HUMAN SPINAL CORD TRIGGERED BY A SUPRASENSIBLE STIMULUS THROUGH THE USE OF FUNCTIONAL NEAR-INFRARED SPECTROSCOPY

FIELD OF INVENTION

The invention consists of a medical device to obtain and characterize the hemodynamic response of the spinal cord to the presence of suprasensory stimulus. The device allows non-invasive evaluation of local vascular changes generated by the spinal cord in response to electrical stimulation of a peripheral nerve. The device object of this invention allows to evaluate the functionality of the spinal cord, providing relevant information in the vast majority of its alterations allowing to make a diagnosis of its function and its alterations.

BACKGROUND

The present invention consists of a medical device which allows the evaluation and diagnosis of spinal cord functionality, through the characterization of the spinal cord's hemodynamic response thereof as response (neurovascular coupling) to suprasensory stimuli, by the use of functional near-infrared spectroscopy (fNIRS). The device consists of three main components, an electrical stimulator, an optical recording unit and a command and signal processing module. The invention also comprises a method, the clinical protocol and the normal reference statistical values corresponding to the use of the device and monitoring of spinal function. The associated method applies an electrical stimulus to a sensitive nerve in the patient's wrist or ankle at non-painful intensity, which activates the spinal cord generating a local vasodilation response which is extended to the peri-spinal vascular territory, which is optically recorded by sensors that are comfortably attached to the skin of the back. The device object of this invention evaluates the spinal neurovascular coupling, which can be affected in various pathologies such as trauma and spinal sections, intramedullary tumors, degenerative and demyelinating diseases, chronic pain and conditions of spinal neuronal hyperexcitability, arteriosclerosis, aortic aneurysm, arterial hypertension, diabetes, central and peripheral neuropathies, as well as in cases of use of drugs such as anti-inflammatory, anti-epileptic, antiarrhythmic and related with the ability to modify the spinal neuronal excitability or the vascular smooth muscle fiber. In order to better illustrate the invention, the present document describes its application to only a few cases, however, these examples should not be considered as unique or limiting to the broad applications of the invention which have already been mentioned.

Today's optical methods offer non-invasive diagnostics with real-time techniques to measure some important physiological variables. In recent years, the research has focused on the development of non-invasive optical methods based on functional near-infrared spectroscopy (fNIRS) which have demonstrated their diagnostic ability by providing real-time information about the various physiological and pathological processes that occur in tissues and organs mainly based on the differential spectral properties of hemoglobin. This technology allows the study of physiological variables such as oxygen saturation, oxygenation index and blood perfusion in any tissue, allowing its application in medicine for the identification of ischemia processes of any etiology and as well as for the measurement of the modification of blood flows dependent on local tissue metabolic activity. The application of this technology also allows the detection of tumors and the determination of the vascularization of extremities, among others.

The device object of this invention allows to evaluate, in a non-invasive way, the local vascular changes in different regions of the spinal cord and peri-medullary regions as a consequence of the spinal cord neuronal activation induced by an electrical stimulus applied to a peripheral nerve. There is currently no device capable of recording this type of spinal cord signal. It is a functional, non-invasive, harmless, portable, home-based technique with low cost compared to computerized axial tomography and magnetic resonance studies focused mainly on structural information. The functional evaluation of the spinal cord provides relevant information in the vast majority of its alterations, among them (traumatic, vascular, degenerative, compressive and neuropathic, among others). These alterations may be due to a primary alteration of either the nerve cells of the spinal cord, the spinal cord vascular and peri-medullary vascular network, or a set of both types of lesions. The device object of this invention, not only extends the application of the functional near-infrared spectroscopy technique of what is currently known which is the cerebral cortex to the spinal cord, but also serves as a vascular response to sensory activation of the spinal cord, which increases its diagnostic value.

To evaluate the merits of the invention described in this document, a brief summary of the most relevant documents of the proposed technique is presented. In general, in the current knowledge review, no explicit references were found to the determination of the hemodynamic response of the spinal cord using the proposed technology. However, some documents describing related inventions were found. Among them, Document US2010268096 (A1) is considered the most relevant. This document describes a method and apparatus to evaluate the hemodynamic and functional status of the brain.

The method and apparatus described in US2010268096 (A1) include non-invasive measurement of intracranial pressure, evaluation of electrical activity of the brain, and measurement of cerebral blood flow. In general, the method described in patent US2010268096 (A1) differs from the present invention, since said patent determines the hemodynamic and functional state of the brain by measuring intracranial pressure using impedantiometry, electroencephalography and intracranial vascular volume changes with near-infrared spectroscopy (NIRS) and it does not describe the use of said method for the diagnosis of spinal cord damage or alterations nor the hemodynamic response thereof. In contrast, the device object of this invention determines the vascular response due to the neurovascular coupling of the spinal cord, as a result of a suprasensory electrical stimulus, using NIRS technology, resulting in a different invention and method.

Other related documents are US2016015316 (A1), CN104068829(A) and US2009234236 (A1). The first document describes a method for recognizing pain in a non-receptive patient which comprises to obtain imaging data from functional near-infrared spectroscopy (fNIRS) of the cerebral cortex. This method uses the comparison of patterns to detect pain in a patient, being different from the method proposed in the present invention wherein fNIRS is used to determine the spinal vascular response (neurovascular coupling) to an electrical stimulus, to diagnose a possible spinal cord damage. The invention CN104068829(A) discloses an invasive system and a method for detecting nerve cell activity in a spinal cord injury. This method requires prior knowledge of the location of spinal cord damage and surgical access to the site of injury by exposing the spinal cord which should be maintained under controlled conditions of humidity and temperature. This method does not use hemodynamic parameter measurement for diagnosis. Finally, US2009234236 (A1) describes a method for visualizing nerves by observing the hemodynamic response of blood flow to a stimulus in a surgical field. It consists of producing a processed image based on a comparison between the pre-stimulus image and the post-stimulus image. Using this method, the hemodynamic response associated to an electrical stimulus applied to the nerves within a surgical field with application in the cerebral cortex can be evaluated, systems and methods for visualizing the nerve trunks are described, observing the hemodynamic response of the blood flow, however, it does not detail the use of functional near-infrared spectroscopy (fNIRS) nor its application to evaluate spinal cord functionality.

In summary, there are no documents in the state of art, which explicitly describe the obtaining and characterization of the hemodynamic response (neurovascular coupling) of the spinal cord in the presence of suprasensory stimuli and which can provide relevant information on the functionalism of the human spinal cord.

A BRIEF DESCRIPTION OF FIGURES

FIG. 1. Vascular response of the spinal cord to a test electrical stimulus. The vascular response of the spinal cord recorded by a prototype in 1 volunteer, recorded simultaneously at the level: A) cervical (upper panel) and b) lumbar (lower panel) is shown. The graphs represent the concentration of on/hemoglobin as a function of time in response to an electrical stimulus applied to the median nerve (inner face of the left wrist) or the posterior tibial nerve (inner face of the left ankle).

BRIEF DESCRIPTION OF THE INVENTION

The invention consists of a device to evaluate hemodynamic response generated by the spinal cord in response to a suprasensorial stimulus applied to a peripheral nerve (medium or posterior tibial) by the use of functional near-infrared spectroscopy (fNIRS). The device consists of 3 main components, an electrical stimulator, an optical recording unit and a control and signal processing module. The device allows non-invasive, comfortable, harmless, portable, home-based, and low-cost evaluation of changes in local hemodynamic parameters in response to neuronal activation of the spinal cord by electrical stimulation of a peripheral nerve. To do this, infrared photoreceptors are placed on the back, at the level where the hemodynamic alteration is desired to be observed, and thus information can be obtained which allows a diagnosis and to determine if there is any alteration or spinal cord damage. The invention also comprises a corresponding method of using the device and monitoring the spinal function.

DETAILED DESCRIPTION OF THE INVENTION

The invention consists of a medical device to obtain and characterize the hemodynamic response of the spinal cord to the presence of suprasensory stimulus. The device consists of the following parts:

A) Stimulation Module:

A battery-powered electronic circuit capable of generating controlled electrical pulses in amplitude (0 to 50 mA), duration (0 to 5 ms) and frequency (0 to 200 Hz) with connection to a bipolar electrode (40 mm interelectrode distance) and a grounding electrode. This module allows stimulation pulses to be applied directly to the skin and through it to the peripheral nerve (medium or posterior tibial). The control module allows to program the stimulation pattern and parameters to be used during the procedure.

B) Spectroscopic Recording Module:

It consists of a regulated, stabilized, LED-based (light emitting diode) light source with intensity of 200 to 400 mW which alternately generates light at two wavelengths between 700 and 800 nm (spectral peak of hemoglobin [Hb]) and between 800 and 900 nm (spectral peak of oxyhemoglobin [HBO2]) by a pattern of short-duration (1 to 5 ms) and alternating pulses for each wavelength. The LED is placed in close contact with the skin of the back on the spine at the selected level, a flat-convex lens embedded in a protective cylinder with the LED, allows a homogeneous pattern of tissue illumination formed by at least one emitter optode. Around the emitter optode(s), at a distance of 2.0 to 5.0 cm, at least one receptor optode is fixed, which is (are) intended to capture infrared light dispersed by tissues by photodiodes with specific frequency responses in ranges between 700 to 800 nm and 800 to 900 nm corresponding to Hb y $HbO_2$, generating a direct current potential proportional to the intensity of the infrared beam for each wavelength. The optodes (emitter(s) and receptor(s)) are adjusted perpendicular to the skin on the spine using a flexible polymer rubber band which can be placed by clinical adhesive at any level of the spine (spinal cord) from the cervical segments to the last thoracic vertebral segments corresponding to the lumbo-sacral spinal cord. In a specific mode, the optode(s), either emitters or receivers, can be placed in a carrier band.

C) Signal Control, Processing and Presentation Module:

The infrared emission pattern is controlled by a microprocessor with a feedback handle to ensure the constancy and spectral purity of the emitted light beam. The detected signal generated by the photodiode is analogue/digitally converted to a frequency of 10 Khz and then processed using the modified Beer-Lambert equation including calibration, filtering and normalization algorithms. The results are presented by real-time graphs of the temporal course of signals from all sites simultaneously recorded at the 2 wavelengths (Hb and $HbO_2$). The amplitude versus time graphs of the spinal response to electric stimulus can be viewed separately or superimposed from each recorded spinal level and wavelength.

In the context of the present invention, an optode corresponds to any optical sensor applied to a tissue. This designation is used to differentiate them from the electrode term used for the sensor which captures electrical potentials in the tissues. In the case of the present invention, these optodes are configured to be sensitive to the spectral ranges of hemoglobin. There are several types of optodes: photoresistors (change resistance with the light it picks up), phototransistors (change current amplification with the light it picks up), photodiodes (change current conduction with the light it picks up), photocells (generate current with the light it picks up). In the present invention, photodiodes are preferably used as they have the highest sensitivity to light and the highest spectral specificity in the range of Hb and $HbO_2$ In a preferred embodiment, mounting the device in its simplest form, connects an electrode over a peripheral nerve such as the wrist or ankle or other area of the body whose sensitive nerves correspond to the spinal level wherein the hemodynamic response of the cord is to be evaluated).

In a preferred embodiment the electrodes are applied directly to the skin using conductive gel and fixed with clinical adhesive.

In a particular embodiment the appropriate stimulation parameters are pulses in the range of 0 to 5 ms; 5 to 20 mA and 0.0001 to 0.5 Hz as nominal values.

In a particular embodiment the carrier band of the optodes or more than one band of optodes can be positioned horizontally to evaluate right/left spinal asymmetry.

In another particular embodiment the carrier band of the optodes can be positioned vertically to evaluate intersegmental responses (cervical-dorsal, cervicolumbar, dorsolumbar) of the spinal cord.

In a preferred embodiment one to ten infrared sensors can be placed along the column.

In another preferred embodiment the device can be built as an integral and transportable system which could constantly record the vascular response.

In a preferred embodiment the device is used to obtain relevant information in the diagnosis of various spinal cord disorders, including traumatic, vascular, degenerative, compressive and neuropathic injuries.

EXAMPLES

Following, embodiment examples are included for this invention as described above:

Example 1

Use of a prototype device to record the vascular response of the cervical and thoracic spinal cord to a test electrical stimulus of the median nerve at the level of the inner face of the left wrist.

Description of the Experiment:

A prototype of the device object of this invention was used to record the vascular response of the spinal cord in 1 voluntary subject. Peripheral nerve stimulation consisting of a single pulse of 10 mA intensity, applied to the median nerve or posterior tibial nerve, was applied to evaluate the cervical or lumbar region of the spine, respectively. The vascular response or change in hemodynamic parameters in the evaluated spinal cord regions were recorded for 360 seconds and the obtained data was ploted.

Results:

The obtained results show that peripheral nerve stimulation with a single pulse, with an intensity of 10 mA, applied to the median nerve or posterior tibial nerve, generates at the corresponding metameric level of the spinal cord a neuronal activation that triggers an increase of the regional perimedullary blood flow. Associated with this increase in regional blood flow, there is an increase in oxyhemoglobin concentration and a reduction in deoxyhemoglobin which begins approximately 5 seconds after the application of the pulse with a rapid rise phase and a slower fall phase. In total, the response lasts approximately 30 seconds (FIG. 1).

The invention claimed is:

1. Medical device to obtain and characterize the hemodynamic response of the spinal cord to the presence of suprasensory stimuli wherein the medical device comprises:
   a. a stimulation module;
   b. a spectroscopic recording module which comprises a carrier band with at least one optode, including
      a regulated, stabilized, LED with intensity less than 400 mW or a laser-based light source (Class I, eye safe), which alternately generates light at two wavelengths between 700 and 800 nm and between 800 and 900 nm, using a short-duration (1 to 5 ms) and alternating pulse pattern for each wavelength;
      a flat-convex lens;
      at least one emitter optode;
      at least one receptor optode; and
      adhesion media which allow the spectroscopy recording module to be fixed on the skin of the back; and
   c. a signal processing and presentation control module.

2. Medical device according to claim 1, wherein the stimulation module is an electronic circuit, capable of generating controlled electric pulses in amplitude from 0 to 50 mA, with a duration of 0 to 5 ms and frequency of 0 to 100 Hz with connection to a bipolar electrode and a grounding electrode.

3. Medical device according to claim 2, wherein the electrodes of the stimulation module are configured to place a bipolar electrode on a peripheral nerve.

4. Medical device according to claim 3, wherein the appropriate stimulation parameters which are applied to the electrodes are pulses from 0 to 5 ms; 5 to 50 mA, 0.0001 to 0.5 Hz as nominal values.

5. Medical device according to claim 1, wherein the LED or laser-based light source allows placing it in close contact with the skin of the back on the spine at one or more selected levels, and wherein the receptor and/or emitter optode(s) can be adjusted perpendicular to the skin of the back.

6. Medical device according to claim 1, wherein the adhesion media includes a flexible polymer rubber band which can be placed by clinical adhesive in one or more levels of any place of the back (spinal cord) from the cervical segments to the last thoracic vertebral segments corresponding to the lumbo-sacral spinal cord.

7. Medical device according to claim 1, wherein the flat-convex lens is embedded in a protective cylinder with the LED or a fiber optic tip of the laser based light source, allowing a homogeneous pattern of tissue illumination forming the emitter optode(s).

8. Medical device according to claim 1, wherein the receptor optode(s) are located around the emitter optode(s), which allows the capture of infrared light dispersed by tissues, by photodiodes with specific wavelength between the ranges of 700 and 800 nm and 800 and 900 nm corresponding to Hb and $HbO_2$ generating a potential of direct current proportional to the infrared beam intensity for each wavelength.

9. Medical device according to claim 8, wherein the receptor optode(s) are located at a distance of 2.0 to 5.0 cm from the emitter optode(s).

10. Medical device according to claim 1, wherein the control, processing and presentation of the signal module comprises a microprocessor which controls the emission pattern that guarantees the constancy and spectral purity of the emitted light beam.

* * * * *